(12) United States Patent
Raghukumar et al.

(10) Patent No.: US 6,613,559 B2
(45) Date of Patent: Sep. 2, 2003

(54) SIMULTANEOUS DECOLORIZATION AND DETOXIFICATION OF MOLASSES SPENT WASH USING NOVEL WHITE ROT-LIGNIN-MODIFYING FUNGUS *FLAVODON FLAVUS*

(75) Inventors: Chandralata Raghukumar, Goa (IN); Mysore Srinivasamurthy Shailaja, Goa (IN)

(73) Assignee: Council of Scientific and Industrial Research, New Delhi (IN)

( * ) Notice: Subject to any disclaimer, the term of this patent is extended or adjusted under 35 U.S.C. 154(b) by 13 days.

(21) Appl. No.: 09/810,706

(22) Filed: Mar. 19, 2001

(65) Prior Publication Data

US 2001/0031493 A1 Oct. 18, 2001

Related U.S. Application Data

(63) Continuation-in-part of application No. 09/456,559, filed on Dec. 8, 1999, now Pat. No. 6,395,534.

(51) Int. Cl.$^7$ ............................. B04B 3/00; C12N 1/12
(52) U.S. Cl. ........................ 435/262.5; 435/254.1; 435/911
(58) Field of Search .................. 435/262.5, 911, 435/254.1

(56) References Cited

PUBLICATIONS

Rattan et al., J. Res. (Punjab Agric. Univ.), (1983 (RECD 1984)) 20 (2), 228–229.

Purkayastha, et al., Proceedings of the Indian National Science Academy Part B Biological Sciences, (1994) vol. 60, No. 3, pp. 269–275.

*Primary Examiner*—Irene Marx
(74) *Attorney, Agent, or Firm*—Smith, Gambrell & Russell, LLP

(57) ABSTRACT

The invention relates to a process for simultaneous decolorization and detoxification of molasses spent wash or water/soil contaminated with molasses spent wash using white-rot lignin modifying fungus strain *Flavodon flavus* which has been deposited at the National Institute of Oceanography, Goa, India, bearing accession No. NIOCC #312 and has also been deposited at ARS Patent collection (NRRL), USDA, Illinois, U.S.A., bearing accession No. 30302.

10 Claims, 4 Drawing Sheets

Figure 1:
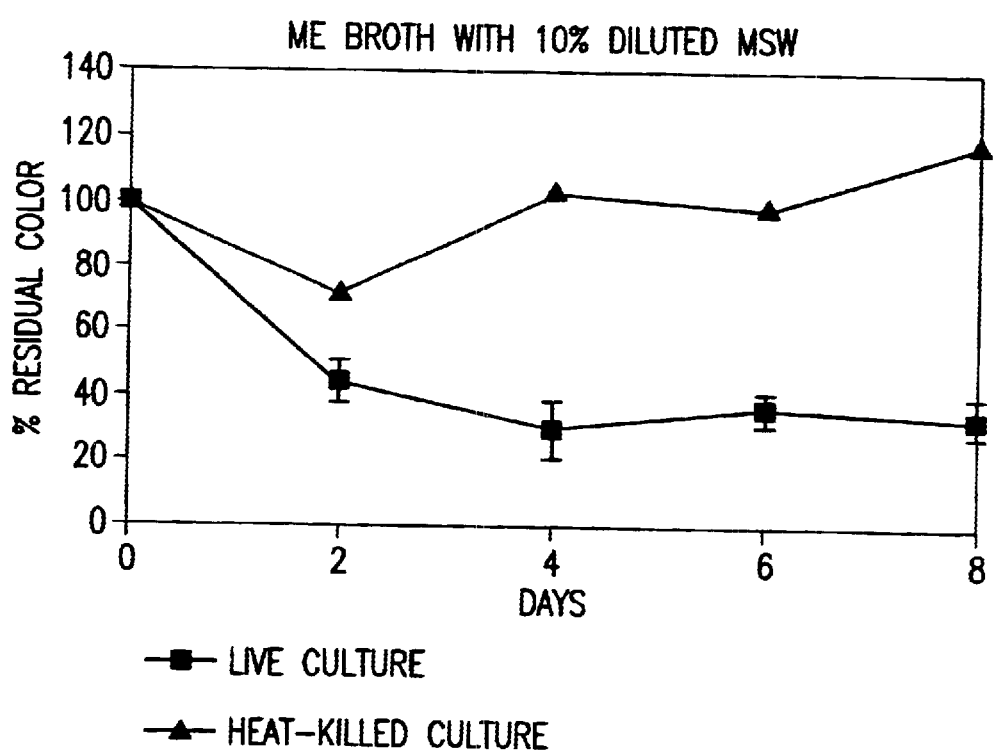

SIMULTANEOUS DECOLORIZATION AND DETOXIFICATION OF MOLASSES SPENT WASH USING NOVEL WHITE ROT-LIGNIN-MODIFYING FUNGUS *FLAVODON FLAVUS*

This application is a continuation-in-part of U.S. Patent Application No. 09/456,559, filed on Dec. 8, 1999, now U.S. Pat. No. 6,395,534, which is hereby incorporated by reference in its entirety.

FIELD OF THE INVENTION

This invention relates to a process for the simultaneous decolorization and detoxification of molasses spent wash using strain of white-rot fungus, "*Flavodon flavus*" having accession No. NRRL 30302. The invention also relates to a novel strain "*Flavodon flavus*" which has been identified and which has been deposited at National Institute of Oceanography, Dona Paula, Goa, India, bearing the accession No. NIOCC #312 and also at Agricultural Research Service Culture Collection (ARS) [Patent collection (NRRL), USDA], 1815 North University Street, Peoria, Ill. 61604, U.S.A., bearing accession No. NRRL 30302 on Mar. 10, 2000.

BACKGROUND OF THE INVENTION

Distilleries in India use sugarcane molasses as the raw material for production of alcohol. The effluents from such distilleries contain large amounts of molasses spent wash (MSW). Molasses spent wash from such plants contain high Biological oxygen demand (BOD) and chemical oxygen demand (COD) and suspended solids. MSW pollutes aquatic ecosystems due to its intense brown color which cuts off light, prevents photosynthesis and causes anaerobic conditions. Next to effluent from paper and pulp mill and tannery, molasses spent wash is a major environmental hazard to land or aquatic sources where they are discharged. Due to the importance attached to prevention of environmental pollution, environmental agencies all over the world are imposing strict regulations for mitigation of pollution from industries. The effluents from distilleries containing colored pigments, high-suspended solids, a high concentration of BOD and COD, besides causing aesthetic damage to sites, are toxic to resident flora and fauna. Wastewater from fermentation plant using sugarcane molasses contains a large amount of a dark brown pigment called molasses melonoidin which is not broken down by usual biological treatments. Melanoidin pigments are the products of "Maillard reaction" between sugars and amino compounds produced on heating (Wedzicha and Kaputo, 1992). Anaerobic digestion of MSW-containing effluents is one of the treatments followed by distilleries and the resulting dark brown sludge is used as a fertilizer. The effluent after such treatment has reduced Chemical Oxygen Demand (COD) and Biological Oxygen Demand (BOD) but is still dark brown in color and is a major problem with distilleries. Removal of such colored pigments in molasses spent wash is termed bioremediation. Color removal in such effluents using terrestrial fungi has been reported (Sirianantapiboon et al. 1988).

Normally, the molasses spent wash wastewater disposal includes physical-chemical treatment, waste-minimization and biological treatment. Biological treatment includes pretreatment with activated sludge of spent wash and treatment in stabilization ponds. Unfortunately, wastewater treatment facilities are often unable to completely remove melanoidin pigments from wastewater and thus contribute to pollution of soil and aquatic habitats. They are even proven to be toxic to aquatic animals (Fitzgibbon et al. 1995). Hence, there is a need for developing an efficient method for the treatment of the molasses spent wash.

PRIOR ART RELATING TO THE INVENTION

Various organisms have been tried for degradation of molasses spent wash in distillery wastewater and bioremediation.

(i) A reference may be made to a publication wherein filamentous fungi of the order *Mycelia Sterilia* were screened for decolorization of molasses pigments (Sirianuntapiboon, et al. 1988). The maximum decolorization was achieved within 7–8 days.

(ii) A reference may be made to a publication wherein a thermophilic strain of *Aspergillus fumigatus* G-2-6 was shown to decolorize molasses melanoidin to an extent of 75% at 45° C. within 3 days with shaking (Ohmomo et al., 1987). Shaking of culture and maintaining higher temperature are two additional requirements and thus have practical limitations on a commercial scale.

(iii) A reference may be made to a publication wherein Artemia larvae have been used for treatment of distillery waste and have shown to decrease B.O.D and C.O.D levels considerably. However, they do not help in decolorizing the molasses spent wash (Rahaman, et al., 1992).

(iv) A reference may be made to a publication wherein the melonoidins prepared from a glucose-glycine system are decolorized and degraded on ozone treatment. (Kim and Park 1986). However, this process is expensive and not practical.

(v) A reference may be made to a publication wherein about 85% color from molasses spent wash (MSW) was removed after 10 days by the white-rot fungus *Phanerochaete chrysosporium* grown in a medium containing 6.25% MSW (Fahy et al. 1997). However, *Flavodon flavus*, strain NIOCC 312 used in our studies removes 90% color after 10 days in a medium containing 10% MSW.

(vi) A reference may be made to a publication wherein strain Ps4a of *Trametes versicolor*, a white-rot fungus, yielded about 79% color removal of molasses pigment by day 4 (Aoshima et al. 1985) in a medium containing 10% melanoidin pigments. However, they have used wastewater treated with activated sludge and not raw molasses spent wash from a distillery as the applicants have done in their studies. Moreover, the applicant's isolate is capable of growth and decolorization of MSW in the presence of sea salts.

(vii) A reference also may be made to the applicant's own co-pending U.S. patent application Ser. No. 09/456,559 titled "Novel white rot-lignin-modifying fungus *Flavadon flavus* and a process for removing dye from dye containing water or soil using the fungus" filed on Dec. 7, 1999, wherein the novel fungus "*Flavadon flavus*" has been isolated, identified and was used for the decolorization of the effluents from the textile, leather and paper industries, containing synthetic dyes comprising azo, heterocyclic and polymeric dyes.

The applicants (C.S.I.R.) in their co-pending U.S. patent application Ser. No. 09/456,559 have found out that the fungal isolate *F. flavus* produces lignin-modifying enzymes such as manganese-dependent peroxidase, lignin peroxidase and laccase in conventional natural and synthetic media prepared with distilled water as well as half-strength artificial sea water and also in powdered sugarcane bagasse, pine and spruce wood-powder media. By virtue of these lignin-modifying enzymes which break down a broad range of xenobiotics, this fungus is useful in 80 to 100 percent decolorization of effluents from paper mill, leather industry and wide range of synthetic dyes such as azo dyes, heterocyclic and polymeric dyes within 4 to 6 days. The dyes specifically tested were Azure B, Brilliant green, Crystal violet, Congo red, Remazol Brilliant blue R, Poly B-411 and Poly R-478at 0.02 percent concentration.

The previous application also described growth of the said fungus on a large scale using inexpensive raw materials such as sugarcane baggase suspended in distilled water or half strength artificial sea water. The biomass of the fungus thus obtained can be used for seeding soil contaminated with synthetic dyes. The above study was restricted to decolorization of effluents from paper mills and leather industries and the present application is for the new field of simultaneous decolorization and detoxification of molasses spent wash, which has not been identified so far.

OBJECTS OF THE INVENTION

The main object of the present invention is to develop a method for the simultaneous decolorization and detoxification of molasses spent wash using a novel white-rot lignin modifying fungus strain "*Flavodon flavus*", which has been deposited at National Institute of Oceanography, Dona Paula, Goa, India, bearing the accession No. NIOCC #312 and also at ARS Patent Collection (NRRL), USDA, Illinois, U.S.A., bearing accession No. NRRL 30302.

SUMMARY OF THE INVENTION

To meet the above object, the present invention provides process for the simultaneous decolorization and detoxification of the molasses spent wash using a white rot lignin modifying fungus strain "*Flavodon flavus*", which has been deposited at National Institute of Oceanography, Dona Paula, Goa, India, bearing the accession No. NIOCC #312 and also at ARS Patent Collection (NRRL), USDA, Illinois, U.S.A., bearing accession No. NRRL 30302.

DETAILED DESCRIPTION OF THE INVENTION

Accordingly, the present invention provides a process for the simultaneous decolorization and detoxification of wastewater containing molasses spent wash using white-rot lignin modifying fungus strain *Flavodon flavus*. This application is a continuation application of the co-pending U.S. patent application Ser. No. 09/456,559, filed on Dec. 12, 1999, wherein a novel strain "*Flavodon flavus*" has been identified and claimed, which has been deposited at the National Institute of Oceanography, Goa, India, bearing accession No. NIOCC #312 and has also been deposited at ARS Patent collection (NRRL), USDA, Illinois, U.S.A., and bearing accession No. NRRL 30302 and characteristics such as described here, said process comprising:

(a) growing the white rot strain *Flavodon flavus* in any conventional nutrient medium containing assimilable C and N source, with salinity ranging between 0 to 15 parts per thousand for at least 4 days;
(b) contacting the said bio-mass with waste-waters containing molasses spent wash with oxygenation for a minimum period of 2 to 6 days, and
(c) removing the fungal bio-mass by any conventional method from the wastewater to get water devoid of color and toxicity from molasses spent wash.

Particularly, the present invention relates to degradation of melanoidin pigments and removal of phenols from molasses spent wash waste-water and soil by the fungus *Flavodon flavus* belonging to the class Basidiomycetes deposited at the National Institute of Oceanography, Dona Paula, Goa 403 004, India and bearing the accession number NIOCC 312. The fungus *Flavodon flavus* (isolate NIOCC #312) belonging to the class Basidiomycetes produces fertile basidiomata in a medium containing alpha-cellulose and sometime in malt extract agar medium on a prolonged incubation. It was identified to be *F. flavus* by using the key given by Ryvarden and Johansen (1980). Most of the time this fungus is in non-sporulating form, off white to white in color with slimy looking mycelium and can be recognized by crystals deposited around fungal hyphae.

More particularly, the present invention provides a process for the simultaneous decolorization and detoxification of water/soil contaminated by molasses spent wash.

In an embodiment of the present invention, the carbon source for growing the fungus is selected from the group comprising of glucose, sugarcane bagasse and sugarcane molasses having at least 1 percent concentration.

In another embodiment of the present invention, the concentration of molasses spent wash is between 10 to 50 percent.

In a preferred embodiment of the present invention, the concentration of molasses spent wash is between 10 to 40 percent.

In a more preferred embodiment of the present invention, the concentration of molasses spent wash is between 10 to 25 percent.

In yet another embodiment of the present invention, the nitrogen source is used at low concentration, In yet another preferred embodiment of the present invention, the source is ammonium tartrate at 2.4 mM.

In still another embodiment of the present invention, the age of the said fungal culture is at least 4 days to get maximum decolorization of molasses spent wash.

In one more embodiment of the present invention, the fungal biomass is directly contacted with the raw molasses spent wash.

In one another embodiment of the present invention, the melanoidin pigments of molasses spent wash in distillery wastewater are decolorized by contacting the said fungal biomass.

In an embodiment of the present of the present invention, the toxicity of the molasses spent wash is reduced by 50 percent.

In a preferred embodiment of the present invention, the total phenolics in the raw molasses spent wash are reduced by about 50% by day 6 on treatment with the said fungus.

In yet another embodiment of the present invention, the toxicity of the fungus-treated molasses spent wash to an estuarine fish Oreochromis sp. is absent in contrast to untreated effluent, which showed presence of high concentration of toxic factor responsible for liver damage in the fish and the novel *Flavadon flavus* fungus is capable in removing such high concentration of toxic factor in the molasses spent wash.

In yet another preferred embodiment of the present invention, the damage-causing factor of the molasses spent wash is reduced by 98 percent.

In still another embodiment of the present invention, the Serum serbitol dehydrobenase (SSDH) activity of molasses spent water is reduced from 121.7 units per ml of serum in untreated molasses spent wash to 2.6 units per ml of serum in the molasses spent wash treated with the said fungus.

In one another embodiment of the present invention, the removal of fungal biomass after decolorization and detoxification of molasses spent wash is carried out manually or by filtration.

The said fungus can be grown in synthetic media prepared with distilled water or half-strength seawater. The said fungus can also be grown in conventional media or in powdered sugarcane bagasse suspended in distilled water or half-strength sea water or in 1% sugarcane molasses dissolved in water to raise large biomass of the fungus for large scale field applications for bioremediation of soil or water bodies. The said fungus thus grown can be immobilized by conventional methods and used for removal of color in wastewater containing molasses spent wash.

The organism given in the present invention is a white-rot basidiomycete fungus isolated from decaying marine plant from a coastal marine environment and identified as *Flavodon flavus*. The said fungus *F. flavus* can be grown in malt extract broth containing 3% malt extract and 0.5% peptone in distilled water. The fungal mat grown this way may be macerated and used as starter inoculum for the experimental cultures of synthetic media prepared in distilled water or in half-strength seawater. The synthetic media can be prepared in distilled water or half-strength seawater containing 10% glucose as carbon source, 2.4 mM ammonium tartrate as the nitrogen source, thiamine, trace metal solution, macro element solution containing potassium and magnesium and sodium salts, Tween 80, veratry alcohol and 20 mM sodium acetate buffer at pH 4.5. This medium is referred to as low nitrogen medium. An example for the process for decolorization of molasses spent wash (MSW) involves addition of sterilized, appropriately diluted raw MSW to 4 day old cultures of *F. flavus* growing in various media as described above. The degradation of molasses pigment is monitored spectrophotometrically by removing an aliquot of samples from these cultures and measuring changes in absorbance at 475 nm (Fitzgibbon et al., 1995) every alternate day up to 6 or 8 days. Heat-killed cultures serve as controls where very low decolorization takes place due to adsorption. Moreover, the said fungus can be grown on a large scale using an inexpensive raw material such as sugarcane molasses in distilled water or half-strength sea water.

The said fungus *Flavodon flavus* is capable of growing in the presence of salts whose concentration is similar to that found in half-strength sea water. Most of the industrial effluents from textiles, dyestuff, paper and pulp and leather industries contain chromogenic substances as well as high concentrations of salts, especially chlorides and sulfates (Bartlett, 1971). In light of this, salt tolerant organisms are better suited for such wastewater treatment. Most of the fungi used for bioremediation of such colored wastewater have not been tested for their salt tolerance. In view of this, the present process has an advantage over the conventional processes referred to in various publications discussed above. White-rot fungi are unique among eukaryotic microbes in possessing powerful lignin-degrading oxidative enzymes such as MNP, LIP and lacasses which have a broad substrate specificity and are thus able to oxidize several environmental pollutants. Results from several laboratories have shown that the ability of white-rot fungus such as Phanerochaete chrysosporium to degrade an array of pollutants including MSW is due to the lignin-modifying/degrading enzymes (Reddy, 1995).

BRIEF DESCRIPTION OF THE ACCOMPANYING DRAWINGS

FIG. 1 relates to percentage residual color in ME broth with 10% MSW.

Figure 2A:
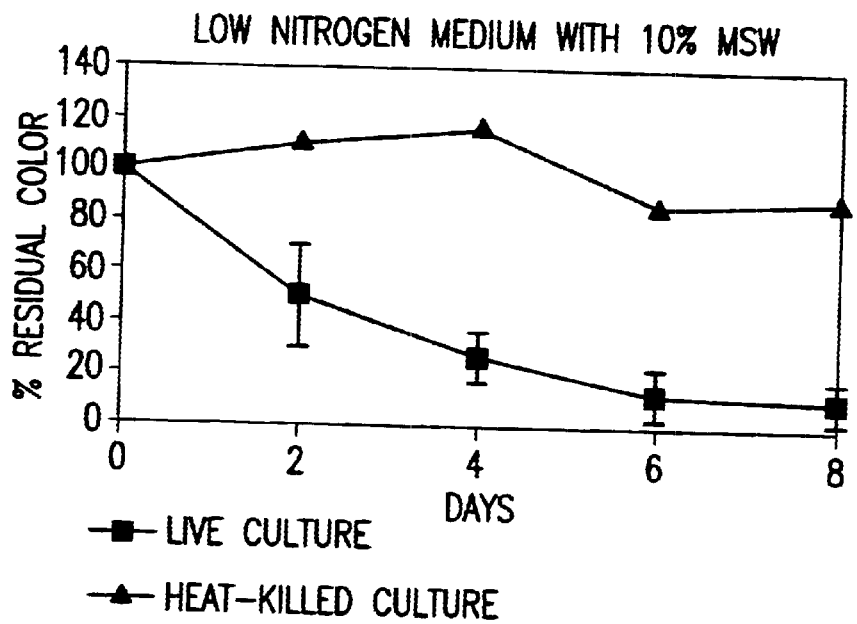

FIG. 2a relates to percentage residual color in low nitrogen medium with 10% MSW.

Figure 2B:
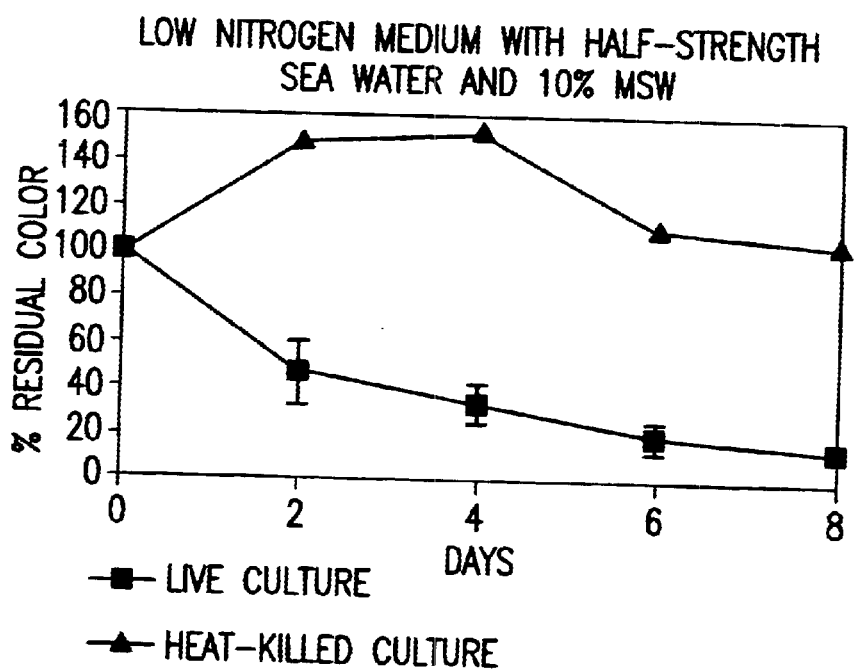

FIG. 2b relates to percentage residual color in low nitrogen medium with half strength seawater and 10% MSW.

Figure 3A:
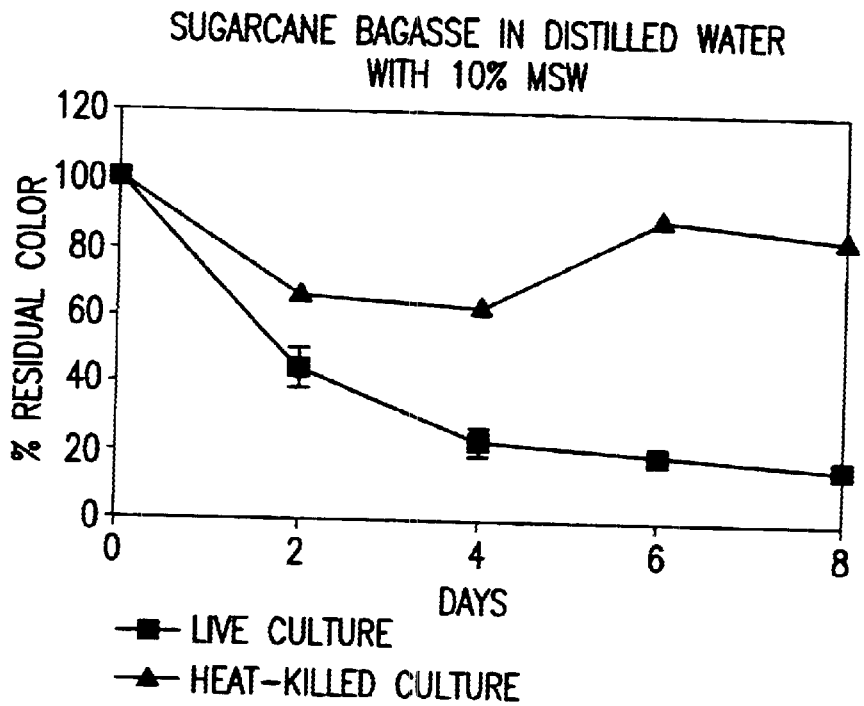

FIG. 3a relates to percentage residual color in sugarcane baggase in distilled water with 10% MSW.

Figure 3B:
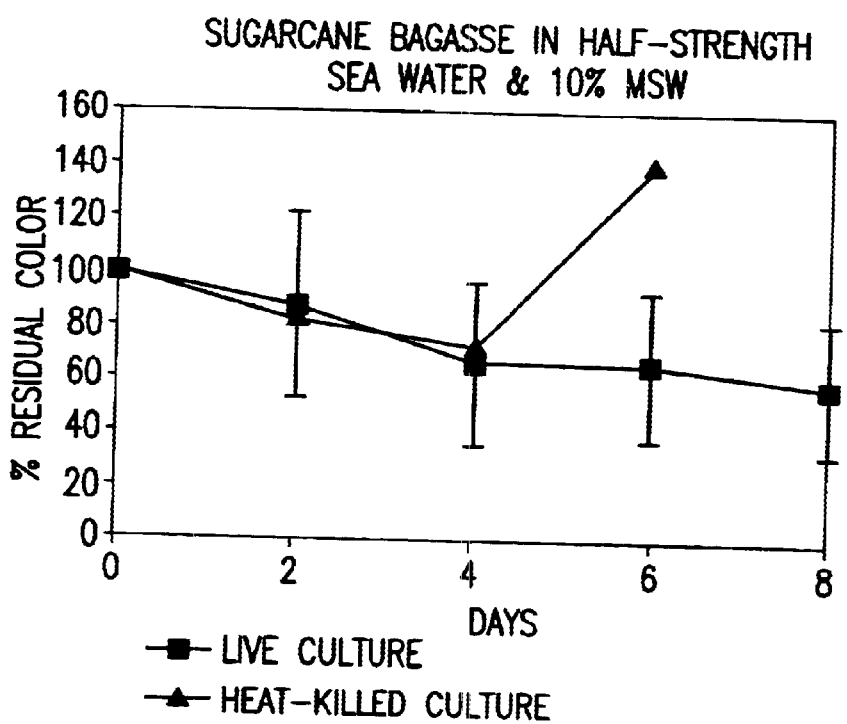

FIG. 3b relates to percentage residual color in sugarcane baggase in half strength seawater and 10% MSW.

Figure 4:
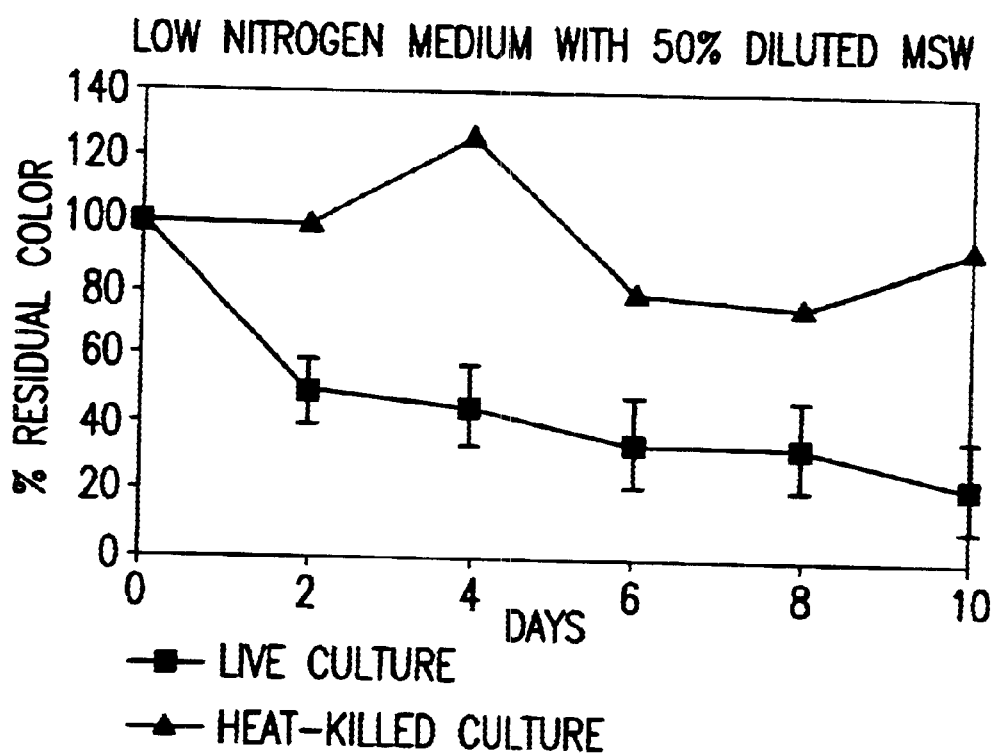

FIG. 4 relates to percentage residual color in low nitrogen medium with 50% MSW.

The invention is described in detail in the examples given below which are provided to illustrate the invention and therefore should not be considered to limit the scope of the present invention.

EXAMPLE 1

Culturing of the Fungus:

The culture *Flavodon flavus*, which been deposited at National Institute of Oceanography, Dona Paula, Goa, India, bearing the accession No. NIOCC #312 and also at ARS Patent Collection (NRRL), USDA, Illinois, U.S.A., bearing accession No. NRRL 30302 was maintained on slants of malt extract agar containing malt extract 30 g; peptone 5 g and agar 15 g $L^{-1}$ water.

For inoculum preparation, mycelial mats grown in low nitrogen medium for 7–10 days at room temperature were homogenised by shaking with sterilised glass beads on a shaker. One ml of this blended mycelium, equivalent to 3 mg dry weight was added to 100 ml flask containing 10 ml of test medium. The flasks were flushed with 100% $O_2$ at the time of inoculation and every other day thereafter. The culture flasks were inoculated at room temperature without shaking. The low nitrogen medium contained glucose (10%), ammonium tartrate (2.4 nM), $K_2HPO_4$, $MnSO_4$, NaCl, trace metal solution, veratryl alcohol, thiamine, Tween 80 (1%) and sodium acetate buffer (20 mM), adjusted to pH 4.5.

EXAMPLE 2

The ability of *Flavodon flavus*, which has been deposited at National Institute of Oceanography, Dona Paula, Goa, India, bearing the accession No. NIOCC #312 and also at ARS Patent Collection (NRRL), USDA, Illinois, U.S.A., bearing accession No. NRRL 30302, to decolorize molasses spent wash in nutrient rich medium such as malt extract broth (ME broth) was tested. ME broth contains 3% malt extract and 0.5% peptone in distilled water. To 9 ml of ME broth having 4 day old culture (raised as described above), 1 ml of sterilized MSW was added (final concentration of MSW being 10%) and the cultures were oxygenated for 1 min. Autoclaved cultures supplemented with MSW served as heat-killed controls. Aliquots (0.5 ml) of culture supernatants from experimental and heat-killed cultures were appropriately diluted and changes in absorbance maximum at 475 nm were measured using a Shimadzu UV-Visible spectrophotometer (Shimadzu, Japan). The results are calculated as the difference in percent decolorization between initial (0 day) readings and day of measurement.

Accordingly, FIG. 1 shows the percentage of residual color of MSW in malt extract broth in live and heat-killed cultures. The isolate NIOCC 312 decolorized up to 90% of MSW within 8 days and about 50% of color were removed within 2 days.

EXAMPLE 3

The ability of *Flavodon flavus*, which has been deposited at National Institute of Oceanography, Dona Paula, Goa, India, bearing the accession No. NIOCC #312 and also at ARS Patent Collection (NRRL), USDA, Illinois, U.S.A., bearing accession No. NRRL 30302 to decolorize molasses spent wash in synthetic medium such as low nitrogen medium prepared with distilled water and half-strength sea water containing 10% glucose as carbon source, 2.4 mM ammonium tartrate as the nitrogen source, thiamine, trace metal solution, macro element solution containing sodium, potassium and manganese salts, Tween 80, veratryl alcohol and 20 mM sodium acetate buffer at pH 4.5. To 9 ml of low nitrogen medium containing 4-day-old culture of *F. flavus*, 1 ml of sterilized raw MSW (final concentration of MSW being 10%) was added and the cultures were treated and absorbance taken as described in the Example 2.

Accordingly, FIGS. 2a and 2b show percentage of residual color in the medium prepared with distilled water and half-strength seawater. By the day 8, about 90% of decolorization were observed in medium prepared with distilled water or half-strength seawater. About 50% of decolorization were achieved on day 2 itself.

EXAMPLE 4

The ability of *Flavodon flavus*, which has been deposited at National Institute of Oceanography, Dona Paula, Goa, India, bearing the accession No. NIOCC #312 and also at ARS Patent Collection (NRRL), USDA, Illinois, U.S.A., bearing accession No. NRRL 30302 to decolorize molasses spent wash in inexpensive simple substrate such as sugarcane bagasse was tested. Powdered sugarcane bagasse (1% weight/volume) was suspended in distilled water or half-strength seawater. To 4 day old culture of *F. flavus* growing in these media, MSW to the final concentration of 10% as described above was added and decolorization monitored as described previously in the Example 2.

Accordingly, FIGS. 3a and 3b show percentage residual color in the medium prepared with distilled water and half-strength seawater using live and heat-killed cultures. By the day 8, about 80% and 50% decolorization was observed in distilled water and half-strength seawater respectively. By day 2, 50% and 20% decolorization was achieved in sugarcane bagasse suspended in distilled water and seawater respectively.

EXAMPLE 5

The ability of *Flavodon flavus*, which has been deposited at National Institute of Oceanography, Dona Paula, Goa, India, bearing the accession No. NIOCC #312 and also at ARS Patent Collection (NRRL), USDA, Illinois, U.S.A., bearing accession No. NRRL 30302 to decolorize higher concentration of molasses spent wash was tested using synthetic medium such as low nitrogen medium. To 4 day old culture of *F. flavus*, MSW to the final concentration of 50% was added and decolorization monitored as described in the Example 2.

Accordingly, FIG. 4 shows about 50% and 80% decolorization by day 2 and 10 respectively.

EXAMPLE 6

Total phenolics in raw untreated and fungus-treated MSW were extracted using 1:1 mixture of ethyl acetate:acetone (Fitzgibbon et al., 1995). The extracts were concentrated in a rotary evaporator at 35° C. Total phenolics were estimated using Folin-Dennis reagent (Swain and Hillis, 1959). Catechol was used as reference standard. Accordingly, there was 50% reduction in total phenolics in fungus-treated molasses spent wash.

EXAMPLE 7

Toxicity Assay:

Serum sorbitol dehydrogenase (SSDH) is a specific indicator of chemically-induced liver damage in fish. SSDH activity was determined with a kinetic ultraviolet spectrophotometric assay at room temperature wherein the rate of conversion of fructose to sorbitol by SDH was followed by measuring the oxidation of the cofactor NADH at 366 nm wavelength (d'Apollonia and Anderson, 1980).

In an estuarine fish *Oreochromis mossambicus* exposed to 1000× diluted, untreated MSW for 4 days, SSDH activity was 121.7 Units $ml^{-1}$ serum.

With fungus-treated MSW at the same dilution, the activity was 2.6 Units $ml^{-1}$ serum. Thus, treatment of the MSW has effected a near total (ca. 98%) removal of the damage-causing factor.

What is claimed is:

1. A process for simultaneous decolorization and detoxification of an effluent containing molasses spent wash or water or soil contaminated with molasses spent wash using white-rot lignin modifying fungus strain *Flavodon flavus* NRRL 30302, said process comprising:
    (a) growing the white-rot strain of *Flavodon flavus* in a nutrient medium containing assimilable C and N source, with salinity ranging between 0 to 15 parts per thousand, for at least 4 days;
    (b) contacting the resulting fungal bio-mass with molasses spent wash or water or soil contaminated with molasses spent wash for a minimum period of 2 days; and
    (c) removing the fungal bio-mass to get the spent wash, water or soil devoid of color and toxicity imparted by the molasses spent wash.

2. The process as claimed in claim 1, wherein the carbon source for growing the fungus is selected from the group consisting of glucose, sugarcane bagasse and sugarcane molasses having at least 1% concentration.

3. The process as claimed in claim 1, wherein the nitrogen source is ammonium tartrate at 2.4 mM concentration.

4. The process as claimed in claim 1, wherein the concentration of molasses spent wash in the effluent is between 10 to 60 percent vol/vol.

5. The process as claimed in claim 1, wherein the concentration of molasses spent wash in the effluent is between 10 to 50 per cent vol/vol.

6. The process as claimed in claim 1, wherein the concentration of molasses spent wash in the effluent is between 10 to 25 per cent vol/vol.

7. The process as claimed in claim 1, wherein melanoidin pigments of the molasses spent wash are decolorized by contacting the said fungal biomass.

8. The process as claimed in claim 1, wherein the total phenolics in the molasses spent wash are reduced by about 50% by day 6 on treatment with the said fungus.

9. The process as claimed in claim 1, wherein the fungus-treated molasses spent wash is less toxic to an estuarine fish as compared to an untreated molasses spent wash.

10. The process as claimed in claim 1, wherein the removal of fungal biomass after decolorization and detoxification of molasses spent wash is carried out by filtration.

* * * * *

UNITED STATES PATENT AND TRADEMARK OFFICE
CERTIFICATE OF CORRECTION

PATENT NO. : 6,613,559 B2
DATED : September 2, 2003
INVENTOR(S) : Chandralata Raghukumar et al.

It is certified that error appears in the above-identified patent and that said Letters Patent is hereby corrected as shown below:

<u>Title page,</u>
Item [30], Foreign Application Priority Data, please insert:
-- (30) Foreign Application Priority Data
Mar. 31, 1999   (IN)………………..494/DEL/99 --

Signed and Sealed this

Sixth Day of July, 2004

JON W. DUDAS
*Acting Director of the United States Patent and Trademark Office*